US012594314B2

(12) United States Patent
Nowak et al.

(10) Patent No.: US 12,594,314 B2
(45) Date of Patent: Apr. 7, 2026

(54) PROCESS AND APPARATUS FOR PRODUCTION OF A GRANULAR CANNABINOID MATERIAL ESSENTIALLY SOLUBLE IN AQUEOUS MEDIUM

(71) Applicant: ADD Advanced Drug Delivery Technologies Ltd., Pratteln (CH)

(72) Inventors: Mirko Nowak, Loerrach (DE); Michael Jacob, Weimar (DE)

(73) Assignee: ADD Advanced Drug Delivery Technologies Ltd., Pratteln (CH)

( * ) Notice: Subject to any disclaimer, the term of this patent is extended or adjusted under 35 U.S.C. 154(b) by 841 days.

(21) Appl. No.: 17/629,867

(22) PCT Filed: Jun. 23, 2020

(86) PCT No.: PCT/EP2020/067401

§ 371 (c)(1),
(2) Date: Jan. 25, 2022

(87) PCT Pub. No.: WO2021/018479

PCT Pub. Date: Feb. 4, 2021

(65) Prior Publication Data

US 2022/0273744 A1     Sep. 1, 2022

(30) Foreign Application Priority Data

Jul. 26, 2019    (DE) ..................... 10 2019 211 195.5

(51) Int. Cl.
| | |
|---|---|
| *A61K 36/185* | (2006.01) |
| *A61K 9/16* | (2006.01) |
| *A61K 31/00* | (2006.01) |
| *B01J 8/18* | (2006.01) |
| *B01J 8/24* | (2006.01) |

(52) U.S. Cl.
CPC ........ *A61K 36/3482* (2024.05); *A61K 9/1694* (2013.01); *A61K 31/658* (2023.05); *B01J 8/1818* (2013.01); *B01J 8/24* (2013.01); *B01J 2204/002* (2013.01); *B01J 2204/005* (2013.01)

(58) Field of Classification Search
CPC .............. A61K 36/3482; A61K 9/1694; A61K 31/658; B01J 8/1818; B01J 8/24; B01J 2204/002; B01J 2204/005
See application file for complete search history.

(56) References Cited

U.S. PATENT DOCUMENTS

| | | | |
|---|---|---|---|
| 5,656,289 A | 8/1997 | Cho et al. | |
| 6,383,513 B1 * | 5/2002 | Watts ................... | A61K 31/352 |
| | | | 424/455 |
| 7,585,538 B2 | 9/2009 | Mangos et al. | |
| 10,328,216 B2 | 6/2019 | Boeckl et al. | |
| 2010/0226994 A1 | 9/2010 | Hirai et al. | |
| 2011/0039002 A1 | 2/2011 | Verkoeijen et al. | |
| 2016/0143972 A1 | 5/2016 | Stebbins et al. | |
| 2016/0367522 A1 * | 12/2016 | De Vries .............. | A61K 9/2018 |
| 2019/0022009 A1 | 1/2019 | Luna et al. | |

FOREIGN PATENT DOCUMENTS

| | | |
|---|---|---|
| AT | 509000 A1 | 5/2011 |
| CN | 107080145 A | 8/2017 |
| DE | 10326231 A1 | 2/2005 |
| DE | 102016121050 A1 | 5/2017 |
| EP | 2298284 A2 | 3/2011 |
| JP | 2000334288 A | 12/2000 |
| JP | 2002219349 A | 8/2002 |
| JP | 2005525093 A | 8/2005 |
| JP | 201272190 A | 4/2012 |
| JP | 2019507125 A | 3/2019 |
| WO | 9932107 A1 | 7/1999 |
| WO | 02064109 A2 | 8/2002 |
| WO | 2018204326 A1 | 11/2018 |

OTHER PUBLICATIONS

English-language Translation of the Office Action from the United Arab Emirates Patent Office for related Application No. P6000143/2022.
Patel, Vivek, et al. Lipid-based oral formulation strategies for lipophilic drugs. AAPS PharmSciTech, 2018, 19. Jg., Nr. 8, S. 3609-3630.

* cited by examiner

*Primary Examiner* — Shirley V Gembeh
(74) *Attorney, Agent, or Firm* — The Webb Law Firm

(57) ABSTRACT

A process and to an apparatus for production of a granular cannabinoid material essentially soluble in aqueous medium, wherein a matrix liquid composed of a first liquid that dissolves a cannabinoid or composed of a first liquid that dissolves a cannabinoid and a second liquid that forms an emulsion with the first liquid and a cannabinoid dissolved in the first liquid or emulsion is produced. The matrix liquid is dried by convection, and wherein the apparatus has a vessel system having an inlet and a matrix liquid outlet for production of the matrix liquid and a drying apparatus fluidically connected to the matrix liquid outlet of the vessel system.

19 Claims, 4 Drawing Sheets

PROCESS AND APPARATUS FOR PRODUCTION OF A GRANULAR CANNABINOID MATERIAL ESSENTIALLY SOLUBLE IN AQUEOUS MEDIUM

CROSS-REFERENCE TO RELATED APPLICATIONS

This application is the United States national phase of International Application No. PCT/EP2020/067401 filed Jun. 23, 2020, and claims priority to German Patent Application No. 10 2019 211 195.5 filed Jul. 26, 2019, the disclosures of which are hereby incorporated by reference in their entirety.

BACKGROUND

Field

The invention relates to a method for manufacturing a cannabinoid granulate which is essentially soluble in an aqueous environment, wherein a matrix liquid is manufactured from a first liquid which dissolves a cannabinoid or from a first liquid which dissolves a cannabinoid and a second liquid which with the first liquid forms an emulsion and from a cannabinoid which is dissolved in the first liquid or the emulsion.

Description of Related Art

The invention further relates to an apparatus for manufacturing a cannabinoid granulate which is essentially soluble in an aqueous environment.

Methods and apparatuses for manufacturing in particular oral dosage forms of a cannabinoid have belonged to the state of the art for some time now.

WO 02/064109 A2 discloses pharmaceutical formulations for use on administering lyophilic medications via mucous membrane surfaces. In particular, pharmaceutical formulations are provided for use on administering a lipophilic medication via a mucous membrane surface and on hydration form am emulsion which contains lipophilic medication, in particular medication which as active ingredients contain certain combinations of cannabinoids in predefined ratios, wherein the medication is capable of sticking to a mucous membrane surface and permitting a controlled release of the medication.

A method for manufacturing a solid dosage form of a cannabinoid is disclosed in US 2016/0143972 A1, wherein the solid dosage form of the cannabinoid is essentially soluble in an aqueous solution. The method comprises the dissolving of a cannabinoid and of one or more emulsifiers in one or more solvents, in order to obtain one or more combined solutions and furthermore a drying of the one or more solvents from the one or more combination solutions which comprise solvents, in order to obtain the solid dosage form of the cannabinoid.

The disadvantage is the fact that the solid dosage forms of a cannabinoid which are mentioned in the state of the art have an insufficient systemic absorption and therefore the bioavailability of the cannabinoids is low, since the grain size distribution of the solid dosage forms are not very homogenous and furthermore a poor pourability of the orally dispensed, possibly solid dosage form is given.

SUMMARY

It is therefore the object of the invention to increase the fields of application for consumers and to increase the systemic absorption of the cannabinoids, so that the bioavailability of the cannabinoids improves and to simultaneously improve the pourability of the solid dosage form of the cannabinoids.

Given a method of the initially mentioned type, this object is achieved by way of the matrix liquid being convectively dried. The matrix liquid is preferably spray dried or is convectively dried in a fluidisation apparatus by way of spray granulation, spray agglomeration or spray encapsulation, into a cannabinoid granulate. Surprisingly, it was found that given a convective drying of the matrix liquid which contains the cannabinoid, in a fluidisation apparatus, in particular in a fluidised bed or spouted bed apparatus by way of spray granulation, spray agglomeration or spray encapsulation, a stable emulsion of a first and second liquid forms after a renewed dissolving of the cannabinoid granulate in the aqueous environment, wherein a resorbability of the cannabinoids is significantly improved and an more optimal bioavailability is herewith ensured. The improved resorbability and the more optimal bioavailability of the cannabinoids results from more homogeneous and smaller emulsion particles (oil droplets in water) after the renewed dissolving of the cannabinoid granulates in the aqueous environment compared to the emulsion particles (oil droplets in water) which are contained in the matrix liquid, before the convective drying of the fluidisation apparatus. The dissolving behaviour of the granulate in the aqueous environment is also improved in comparison to conventional products such as a pellet. Furthermore, a reduction of the average diameter x as well of the equivalent diameter after the convective drying in the fluidisation apparatus was surprisingly ascertained. The cannabinoid granulates can be filled very easily in stickpacks or pressed into tablets or processed further in capsules.

Transformation products and synthetic analogues of some terpenphenols are denoted as cannabinoids. Endogenous substances which have similar pharmacological characteristics as cannabinoids, so-called endo-cannabinoids, and substances of plants other than hemp plants which have a similar or equal effect as cannabinoids, so called phyto-cannabinoids are denoted here as cannabinoids. For example, the cannabinoid can comprise one or more of cannabidiol (CBD), cannabinol (CBN) and Δ9-tetrahydrocannabidol (THC) or others.

According to a further development of the method with regard to this, firstly a cannabinoid is dissolved in a first liquid and the first liquid subsequently mixed with the second liquid for forming the emulsion.

Furthermore, concerning the embodiment of the method with regard to this, the first liquid is firstly mixed with the second liquid for forming the emulsion and a cannabinoid is subsequently dissolved in the emulsion.

Preferably, the first liquid consists of the group of lipids, alcohols, oils and/or an arbitrary mixture of these. The selection of the first liquid is of huge significance for example for the resorbability of cannabinoids in the gastrointestinal tract of the human being. Simultaneously, the selection of the first liquid is also significant with regard to a possible masking of the taste. Here, it is particularly oils, such as for example orange oil, which are considered.

Further preferably, the second liquid is an aqueous solution or water.

In a very advantageous embodiment of the method, the first liquid is an oil or a mixture of various oils, in particular rapeseed oil, orange oil or coconut oil, and/or an alcohol or a mixture of various alcohols, in particular ethanol, preferably with a purity of >80%, and the second liquid is water and thus an oil-in-water emulsion or an alcoholic solution.

Excipients for manufacturing and stabilising emulsions are denoted as emulsifiers. Hereby, these are preferably surfactants which serve for blending two liquids which cannot be mixed with one another, such as for example oil and water, into a finely distributed mixture, the so-called emulsion and for stabilising this.

According to an advantageous further development of the method, an emulsifier is added to the second liquid before the mixing with the first liquid.

According to a further development which is of benefit, an emulsifier is added to the emulsion before the convective drying.

Furthermore, an emulsifier is added to the matrix liquid preferably before the convective drying.

The addition of an emulsifier or also of several emulsifiers has the advantage that the first and the second liquid distribute more finely in the emulsion, by which means a matrix liquid which is better suited for the convective drying in a convective drying apparatus, for example a drum drier, a vacuum drier or in particular in a fluidisation apparatus, preferably spouted bed or fluidised bed apparatus can also be manufactured. The addition of the one or more emulsifiers, such as for example Hi-Cap 100 (modified starch) or the like is preferably effected amid stirring, preferably by way of a stirring device or the like and/or under the effect of temperature, i.e., the feed or dissipation of heat.

Furthermore, according to an additional advantageous embodiment of the method, the matrix liquid is homogenised before the convective drying. The emulsion is preferably high-pressure homogenised, particular preferably at pressures between 50 bar and 250 bar, very particularly preferably at pressures between 100 bar and 200 bar, most preferably at pressures between 125 bar and 175 bar. On account of the homogenisation, the average diameter of the droplets of the first liquid which are present in the emulsion is greatly reduced, so that the mixture of the first and second liquid—wherein these are not soluble in one another— becomes more homogeneous, i.e., more uniform. On account of the homogenisation, in particular the high-pressure homogenisation, an optimised matrix liquid for convective drying, in particular in the fluidisation apparatus is produced.

Advantageously, the matrix liquid is deposited onto one or more carrier substances before the convective drying, in particular in a fluidisation apparatus. Preferably, a wet granulate which comprises the cannabinoid is produced given a simultaneously compacting of the carrier substances, by way of the depositing of the matrix liquid onto one or more carriers substances before the convective drying. Preferably, the matrix liquid is extruded after the deposition onto one or more carrier substances, or the matrix liquid is pelleted after the deposition onto one or more carrier substances.

According to an additional advantageous embodiment of the method, carrier particles are provided in the fluidisation apparatus. The carrier particles, in particular for example maltodextrin, mannitol, celluloses, lactoses, xylitol or a mixture of these serve as seeds for the build-up of the cannabinoid granulates. The matrix liquid partly evaporates and spray-dried granulate seeds from the matrix liquid itself arise.

Advantageously, additives are added to the solution, emulsion or matrix liquid before the convective drying. By way of the addition of additives, such as in particular carbohydrates, for example maltodextrin, starch, sugar, for example fructose or saccharine, salts such as magnesium separate, aromas or the like, one can achieve a masking of the smell or of the taste of the cannabinoid granulates. Furthermore, additives can be applied if for example the pressability of the cannabinoid granulates must be adapted on manufacture of tablets or if the release profile of the cannabinoids is to be adapted.

According to a preferred further development of the method, the method is carried out in batches or continuously. By way of the variation of facility and process parameters, the desired end product characteristics such as particle size distribution, dissolving speed, bulk density or residual humidity can be individually and optimally set.

Given an apparatus of the initially mentioned type, the object is achieved by way of the apparatus comprising a vessel system which comprises an inlet and a matrix liquid outlet, for the manufacture of the matrix liquid, and a convective drying apparatus which is fluidically connected to the matrix liquid outlet of the vessel system. The convective drying apparatus is preferably designed as a spray drying device, as a drum drier, as a vacuum drier or as a fluidisation apparatus. Surprisingly, it was found that given a convective drying of the matrix liquid which contains the cannabinoid, in a fluidisation apparatus, in particular in a spouted bed apparatus or fluidised bed apparatus, by way of a spray granulation, spray agglomeration or spray encapsulation, a stable emulsion of the first and second liquid forms after a renewed dissolving of the cannabinoid granulate in the aqueous environment, wherein a resorbability of the cannabinoids is significantly improved and thus a more optimal bio-availability is ensured. The improved resorbability and more optimal bioavailability of the cannabinoids results from the more homogeneous and smaller emulsion particles (oil droplets in water) which are obtained for example by way of spraying on and drying, in particular a film drying, of the matrix liquid onto carrier particles after the renewed dissolving of the cannabinoid granulates in the aqueous environment, in comparison to the emulsion particles (oil droplets in water) which are contained in the matrix fluid, before the convective drying, preferably in the fluidisation apparatus. Furthermore, a reduction of the average diameter x as well as of the equivalent diameter after the convective drying in the fluidisation apparatus was also surprisingly ascertained. The cannabinoid granulates can be filled very well into stickpacks and be applied directly into the oral cavity or added to a glass of liquid or be pressed into tablets or processed further into capsules.

According to an advantageous embodiment of the apparatus, the fluidisation apparatus is designed as a spouted bed apparatus or as a fluidised bed apparatus. In comparison to fluidised bed apparatus, spouted bed apparatus for example permit the atomisation given a very low filled quantity and furthermore on the one hand the high shear forces in the spray regions assist in a uniform liquid film formation and on the other hand minimise the tendency to agglomerate.

Advantageously, the vessel system comprises one or more containers. Preferably, the several containers are at least partly fluidically connected amongst one another. Particularly preferably, the apparatus comprises a first container for the first liquid, a second container for the second liquid and a container for the emulsion. Very particular preferably, the container for the emulsion corresponds to the first or second container. A simple manufacture of the matrix liquid is ensured given starting substances which are to be simultaneously processed in a separate manner.

According to an additional advantageous further development of the preferred apparatus, the convective drying apparatus, preferably the fluidisation apparatus comprises a nozzle for atomising the emulsion or solution. The nozzle, preferably a two-component nozzle is preferably configured to spray particles with a droplet size of 1 μm to 200 μm, preferably of 10 μm to 100 μm, particularly preferably between 20 μm and 60 μm. Very particularly preferably, the spray droplets have a droplet size of 25 μm to 40 μm, most preferably of 30 μm. By way of the adjustment of the particle size by way of the nozzle and the pressurised air, to which the nozzle is subjected, the shear forces which occur on spraying can be set in a precise manner, so that a very homogenous droplet size of the emulsion or solution which is to be sprayed can be targeted or achieved. The droplets settle on the carrier particles, such as cellulose, lactose or xylitol and a film evaporation preferably takes place. On account of the film evaporation, a very uniform evaporation of the emulsion or solution is achieved at the carrier particles.

According to an advantageous further development of the apparatus, a homogeniser for homogenising the matrix liquid is arranged between the vessel system and the drying apparatus, preferably the fluidisation apparatus. By way of the homogenisation, the average diameter of the first liquid which is present in the emulsion is greatly reduced, so that the mixture of the first and second liquid—wherein these are not soluble into one another—becomes more homogeneous, i.e., more uniform. On account of the homogenisation, in particular the high-pressure homogenisation, a matrix liquid which is optimised for convective drying, in particular in the fluidisation apparatus is produced.

Furthermore, concerning a preferred further development of the apparatus, a granulation unit, preferably a wet mixer, particularly preferably a high-shear granulator, a vertical granulator, a rotor disc granulator or the like is arranged between the vessel system and the drying apparatus, for granulating the matrix liquid. According to a further development of the apparatus in respect of this, an extruder for extruding the granulate is arranged subsequently to the granulation unit.

The homogeniser and/or the granulation unit and/or the extruder are preferably fluidically connected to one another.

According to an additional advantageous embodiment of the apparatus, the inlet and the matrix liquid outlet are designed as a vessel system opening. The advantage of such a design of the inlet and the matrix liquid outlet lies in the simple design solution as well as in the simpler sealing.

BRIEF DESCRIPTION OF THE DRAWINGS

The invention is hereinafter explained in more detail by way of the accompanying drawing, these showing FIG. 1 a schematic representation of a first embodiment example of a preferred apparatus for manufacturing a cannabinoid granulate which is essentially soluble in an aqueous environment, FIG. 2 a schematic representation of a second embodiment example of a preferred apparatus for manufacturing a cannabinoid granulate which is essentially soluble in an aqueous environment, FIG. 3 a sum distribution curve and a density distribution curve of oil droplets of an oil-in-water emulsion (with rapeseed oil) before the drying in the spouted bed apparatus, FIG. 4 a sum distribution curve and a density distribution cure of oil droplets of an oil-in-water emulsion (with rapeseed oil) after dissolving the cannabinoid granulates which has been dried in the spouted bed apparatus, in water, FIG. 5 a sum distribution curve and density distribution curve of oil droplets of an oil-in-water emulsion (with coconut oil) before the drying in the spouted bed apparatus, and FIG. 6 a sum distribution curve and a density distribution curve of oil droplets of an oil-in-water emulsion (with coconut oil) after the dissolving of the cannabinoid granulates which have been dried in the spouted bed apparatus, in water.

DETAILED DESCRIPTION

Figure 1:
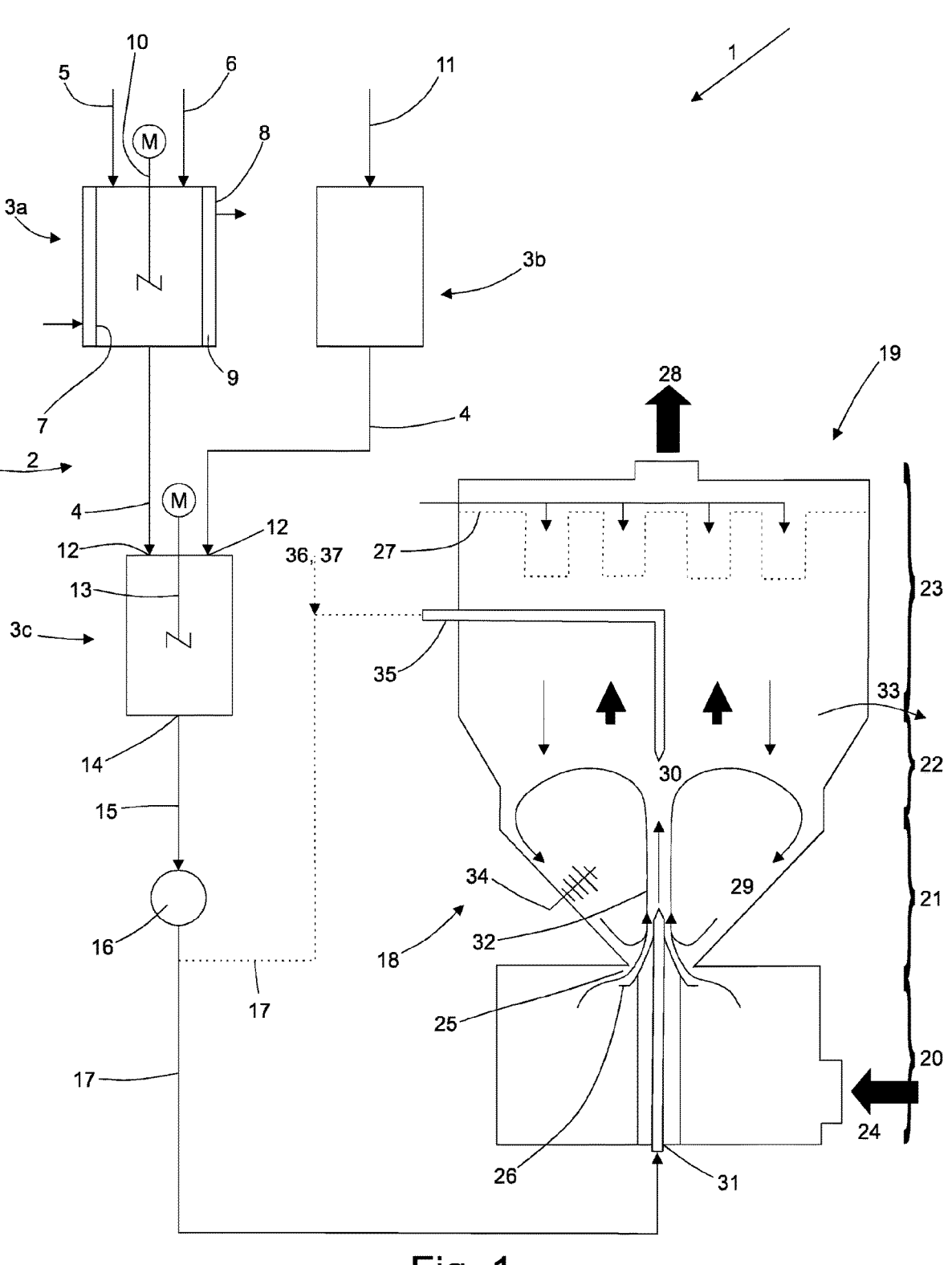

FIG. 1 shows a schematic representation of a first embodiment example of a preferred apparatus 1 for a manufacturing cannabinoid granulate which is essentially soluble in an aqueous environment.

The apparatus 1 comprises a vessel system 2 for manufacturing the matrix liquid. In the embodiment example according to FIG. 1, the vessel system 2 comprises three containers 3, wherein these are fluidically connected amongst one another. The fluidic connection is hereby realised by way of pipe conduits 4.

The first container 3*a* of the vessel system 2 which is designed in a double-walled manner for heating or cooling comprises a cannabinoid inlet 5 and a liquid inlet 6 for a first liquid which consists of the group of lipids, alcohols, oils and/or of an arbitrary mixture of these, in particular however preferably of a rapeseed oil, orange oil or coconut oil.

By way of the container jacket space 9 which is spanned between the container inner wall 7 and the container outer wall 8, the first container 3*a* can be temperature controlled by way of a heating medium which flows through the container jacket space 9*a*. Preferably, the container 3*a* is heated in order to better dissolve a cannabinoid which is possibly not easily soluble, in the first liquid. The temperature control device is not absolutely necessary.

Furthermore, the first container 3*a* comprises a motor-operated stirring device 10 for stirring the first liquid. The stirring device is not absolutely necessary.

The vessel system 2 comprises a second container 3*b* which comprises a liquid inlet 11 for a second liquid, in particular an aqueous solution or water.

The first and second containers 3*a*, 3*b* are each connected to inlets 12 of a third container 3*c* via a pipe conduit 4. The first liquid which contains the cannabinoid, and the second liquid are transported into the third container 3*c* via pipe conduits 4, for example by way of pumps.

The matrix liquid is manufactured in the third container 3*c* by way of mixing the first liquid which contains the cannabinoid and the second liquid, wherein the first and the second liquid form an emulsion with one another. Preferably, this is produced in the third container 3*c* amid stirring by way of a motor-operated stirring device 13. The manufactured matrix liquid leaves the vessel system 2 via a matrix liquid outlet 14, for the manufacture of the matrix liquid.

The matrix liquid can also be manufactured by way of other part-steps, for example, by way of a simple mixing-together of all components in a single container.

The matrix liquid is delivered, for example by way of a pump, via a pipe conduit 15 into a homogeniser 16 for homogenising the matrix liquid, preferably a high-pressure homogeniser. The homogenised matrix liquid is subsequently transported from the homogeniser 16 via the pipe conduit 17 into the fluidisation apparatus 18, for example by way of a pump.

In the embodiment example of FIG. 1, the drying apparatus is designed as a fluidisation apparatus 18 for manufacturing a cannabinoid granulate which is essentially soluble in an aqueous environment, wherein the fluidisation apparatus 18 here designed is as a spouted bed apparatus 19. The construction of the spouted bed apparatus 19 from the bottom to the top comprises a distribution chamber 20, a process space 21, an expansion zone 22 and an exhaust air part 23.

The process gas 24 which is necessary for drying the cannabinoid granulates which are to be manufactured is fed to the distributor chamber 20 where the process gas 24 distributes, and via a gap opening 25 and a process gas deflection part 26 enters into a process space 21 preferably in the manner of a free jet.

Furthermore, the apparatus cross section can optionally enlarge in the expansion zone 22, so that the speed of the process gas flow continuously reduces to the top. The process gas 24 leaves the spouted bed apparatus 19 preferably as an exhaust gas which is purified by way of a dust extraction system 27, in particular filter cartridges or textile filter elements.

Carrier particles, such as for example mannitol, cellulose, xylitol or the like and which are denoted as starter material are located in the process space 21, and these carrier particles are entrained upwards in the direction of the dust extraction system 27 by way of the process gas 24. The process gas speed reduces in the upper region of the process space 21 as well as in the expansion zone 22 which is located thereabove, so that the upwardly flowing carrier particles exit laterally out of the process gas space and fall back into the process space 21. The process space 21 is delimited in the lower region by inclined side surfaces 28. On account of the inclined side surfaces 28, the carrier particles are transported by way of the effect of gravity via the return zone 20 in the direction of the gap opening 25 where they are subsequently entrained again by the process gas 24 into the process space 21.

A very uniform solid matter circulation 30 of the carrier particles forms by way of this mechanism. One or more spray devices 31, preferably a spray nozzle or the like are arranged in the lower region of the process space 21, and these spray upwards in the same direction as the process gas 24 and serve for introducing the matrix liquid. Such an introduction of the matrix liquid in the lower region of the process space 21 is denoted as bottom spray.

The nozzle, preferably a two-component nozzle is configured to spray droplets with a droplet size of 1 µm to 200 µm, preferably of 10 µm to 100 µm, particularly preferably between 20 µm and 60 µm. Very particularly preferably, the sprayed droplets have a droplet size of 25 µm to 40 µm, most preferably 30 µm. By way of setting the droplet size by way of the nozzle and the pressurised air to which the nozzle is subjected, the shear forces which occur on spraying can be set in a precise manner, so that a very homogeneous droplet size of the emulsion or solution to be sprayed can be targeted or achieved. The droplets settle on the carrier particles, such as cellulose, lactose or xylitol and a film evaporation preferably takes place.

On account of the very advantageous heat and substance transmission as well as the high carrier particle circulation in the atomisation region 32 of the process space 21 of the spouted bed apparatus 19, one succeeds in the matrix liquid largely precipitating on the carrier particles and these therefore being wetted at the particle surfaces. The uniform wetting given a simultaneously high particle circulation between the atomisation region 32 and the return zone 28 has the effect of a very uniform liquid film being formed on the carrier particles. On account of the drying process, the matrix liquid evaporates and with the exhaust air 28 leaves the spouted bed apparatus 19. The cannabinoid which is contained in the matrix liquid remains on the particle surface of the carrier particles, so that the arising cannabinoid granulates grow very uniformly and homogeneously.

The output 33 of the cannabinoid granulates can be realised for example by way of an overflow or by way of a volumetric output member, in particular a rotary valve or also be way of a gravity sifter, preferably a zigzag sifter which is subjected to sifting gas or a rising pipe sifter.

Mechanical assemblies 34, such as for example pulverisers, choppers etc. if necessary can also be arranged in the process space 21, preferably in the return zone 29, in order by way of size reduction to generate sufficiently fine particles as granulate seeds for the granulate formation process.

Optionally, one or more spray devices 35 which preferably spray downwards can be arranged in the process space 21 or in the apparatus parts which lie thereabove, the expansion zone 22 and the exhaust air part 23. The fluid matrix liquid can also be atomised into the process space 21 of the spouted bed apparatus 19 via the spray device 35. Alternatively, additives 36 or other components 37 can be sprayed in fluid form by some of the spray devices 31, 35 and thus be homogeneously embedded into the granulate structure.

In the preferred apparatus 1, a granulation unit which is not shown, for granulating matrix liquid can be arranged between the vessel system 2 and the fluidisation apparatus 18 which is designed as a spouted bed apparatus 19. Furthermore, there is the possibility of arranging an extruder for extruding the granulate, subsequently to the granulation unit. Preferably, the homogeniser 16 and/or the granulation unit and/or the extruder are fluidically connected to one another.

Figure 2:
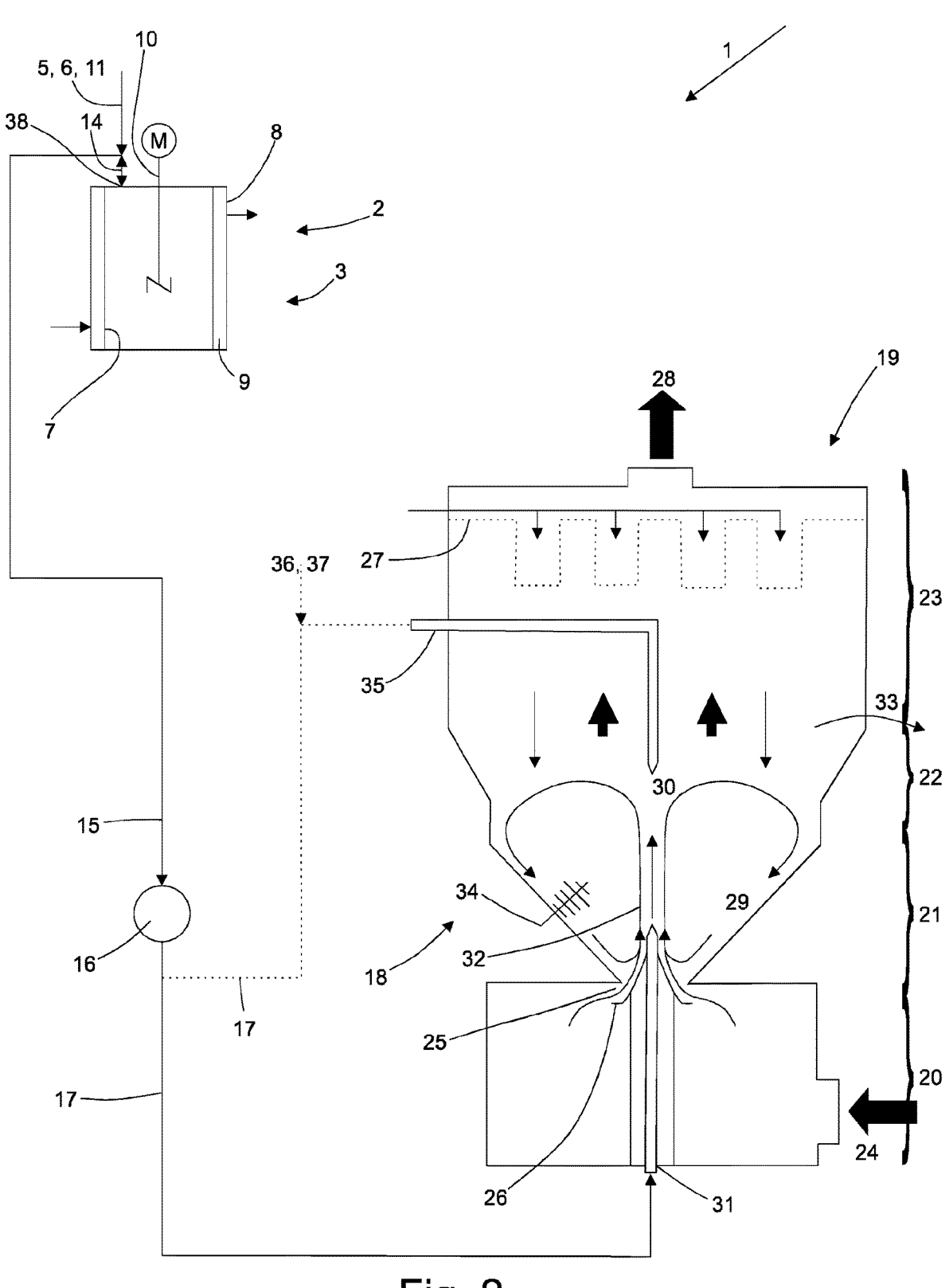

A schematic representation of a second embodiment example of a preferred apparatus 1 for manufacturing a cannabinoid granulate which is essentially soluble in an aqueous environment is shown in FIG. 2.

The apparatus 1 comprises a vessel system 2 for manufacturing the matrix liquid. In the second embodiment example according to FIG. 2, the vessel system 2 comprises a single container 3.

The container 3 of the vessel system 2 which is designed in double-walled manner for heating or cooling has a cannabinoid inlet 5 and a liquid inlet 6 for a first liquid which consists of the group of lipids, alcohols, oils and/or an arbitrary mixture thereof, particularly preferably however of a rapeseed oil, orange oil or coconut oil, as well as a liquid inlet for a second liquid, in particular an aqueous solution or water.

On account of the container jacket interior 9 which is spanned between the container inner wall 7 and the container outer all 8, the first container 3a can be temperature controlled by way of a heating medium which flows through the container jacket interior 9. Preferably, the container 3a is heated in order to better dissolve a cannabinoid which is possibly not very soluble, in the first fluid. The temperature control device is not absolutely necessary.

Furthermore, the first container 3a comprises a motor-operated stirring device 10 for stirring the first liquid. The stirring device is not absolutely necessary.

The matrix liquid is manufactured in the container 3 by way of mixing the first liquid which contains the cannabinoid and the second liquid with one another, wherein the first and the second liquid form an emulsion with one another. Preferably this is produced in the container 3 amid stirring by way of a motor-operated stirring device 13. The manufactured matrix liquid leaves the vessel system 2 for manufacturing the matrix liquid via a matrix liquid outlet 14. The inlet 5, 6, 11 and the matrix liquid outlet 14 are designed as a vessel system opening 38 in the embodiment example.

The matrix liquid is transported, for example by way of a pump, via a pipe conduit 15 into a homogeniser 16 for homogenising the matrix liquid, preferably into a high-pressure homogeniser. The homogenised matrix liquid is subsequently transported, for example by way of a pump, from the homogeniser 16 via the pipe conduit 17 into the fluidisation apparatus 18.

The further convective drying process by way of the fluidisation apparatus is effected according to the first embodiment example which is described in FIG. 1.

Thereafter, the produced cannabinoid granulates can be coated in a drum coater. This has the advantage that the cannabinoid granulates can comprise a coating resistant to gastric juices or a taste masking Examples for the manufacture of a matrix liquid as well as its further processing in the fluidisation apparatus are discussed hereinafter.

Example 1: The manufacture of the cannabinoid granulates in the fluidisation apparatus which is designed as a spouted bed apparatus is effected in charge or batch operation as a bottom spray.

500 g of mannitol was used as a starting material in the fluidisation apparatus.

The matrix liquid has 200 g Hi-Cap 100, 200 g maltodextrin, 1365 g water, 5 g cannabidiol (CBD) and 50 g rapeseed oil. Hereby, the cannabidiol (CBD) was dissolved in rapeseed oil as the first liquid and maltodextrin and Hi-Cap 100 in water as the second liquid. The rapeseed oil containing the CBD and the maltodextrin and water comprising Hi-Cap 100 were subsequently mixed with one another whilst forming an emulsion and the matrix liquid hence manufactured. Maltodextrin and Hi-Cap 100 serve as additives for forming a matrix structure in the matrix liquid.

The spray rates were selected between 10 to 15 g/min. The manufactured cannabinoid granulate dissolved well in water and there formed a stable oil-in-water emulsion. The residual humidity of the cannabinoid granulate was 1.8%

Figure 3:
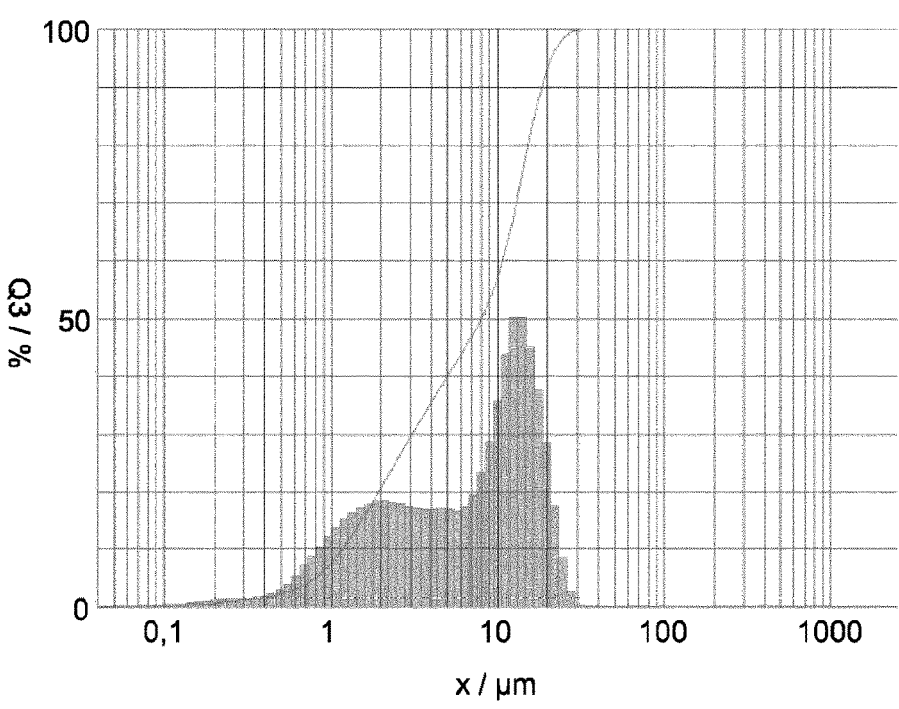

The matrix liquid subsequently to its manufacture was analysed with a laser diffraction system Cilas 1190 LD (Quantachrome). The grain sizes of the CBD containing droplets which are present in the emulsion of the matrix liquid are represented in FIG. 3. The sum distribution curve with equivalent diameters $x_{10}$=1.17 μm, $x_{50}$ O=7.97 μm and $x_{90}$=18.37 μm have an average diameter of x=8.87 μm. Furthermore, the density distribution curve with its two maxima displays a bimodal distribution.

After manufacturing the cannabinoid granulate and a renewed dissolving of the cannabinoid granulate in water, a stable oil-in-emulsion had formed in the aqueous environment.

Figure 4:
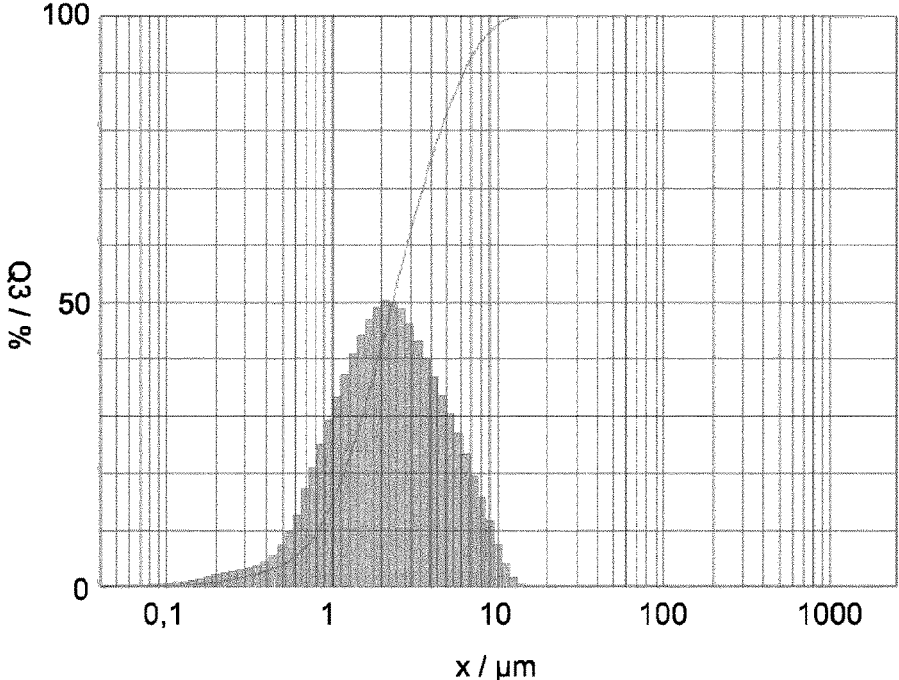

The cannabinoid granulates which are dissolved in the aqueous environment were dissolved in water and again the grain size of the oil droplets containing CBD was analysed with the laser diffraction system Cilas 1190 LD (Quantachrome). FIG. 4 shows the analysis. Hereby, the sum distribution curve with equivalent diameters $x_{10}$=0.82 m, $x_{50}$=2.3 μm and $x_{90}$=6.26 μm has an average diameter of x=3.01 μm. Furthermore, the density distribution curve shows a monomodal distribution. The oil droplets show a very homogenous density distribution with significantly reduced diameters. This leads to a significantly improved resorbability of CBD and thus to a more optimal bioavailability of CBD. This improved resorbability of the cannabinoids results from the more homogeneous and smaller emulsion particles.

Example 2: The manufacture of the cannabinoid granulates in the fluidisation apparatus which is designed as a spouted bed apparatus is effected in charge or batch operation as a bottom spray.

250 g mannitol and 250 g maltodextrin, i.e., in a ratio 1:1 is used as a starting material in the fluidisation apparatus.

The matrix liquid comprises 200 g Hi-Cap 100, 200 g maltodextrin, 1417 g water, 5.5 g cannabidiol (CBD) and 51 g coconut oil. Hereby, the cannabidiol (CBD) was dissolved in coconut oil as a first liquid and maltodextrin and Hi-Cap 100 in water as a second liquid. Subsequently, the coconut oil which contains the CBD and the water which contains the maltodextrin and Hi-Cap 100 were mixed with one another amid the formation of an emulsion and thus the matrix liquid manufactured. Maltodextrin and Hi-Cap 100 hereby serve as additives for forming a matrix structure in the matrix liquid.

The spray rates were increased in comparison to the example 1. Furthermore, the volume flow of the process air was reduced, in order to minimise the product loss at the filters. The manufactured cannabinoid granulate dissolved well in water and formed a stable oil-in water emulsion there. The residual humidity of the cannabinoid granulate was 3.4%.

Figure 5:
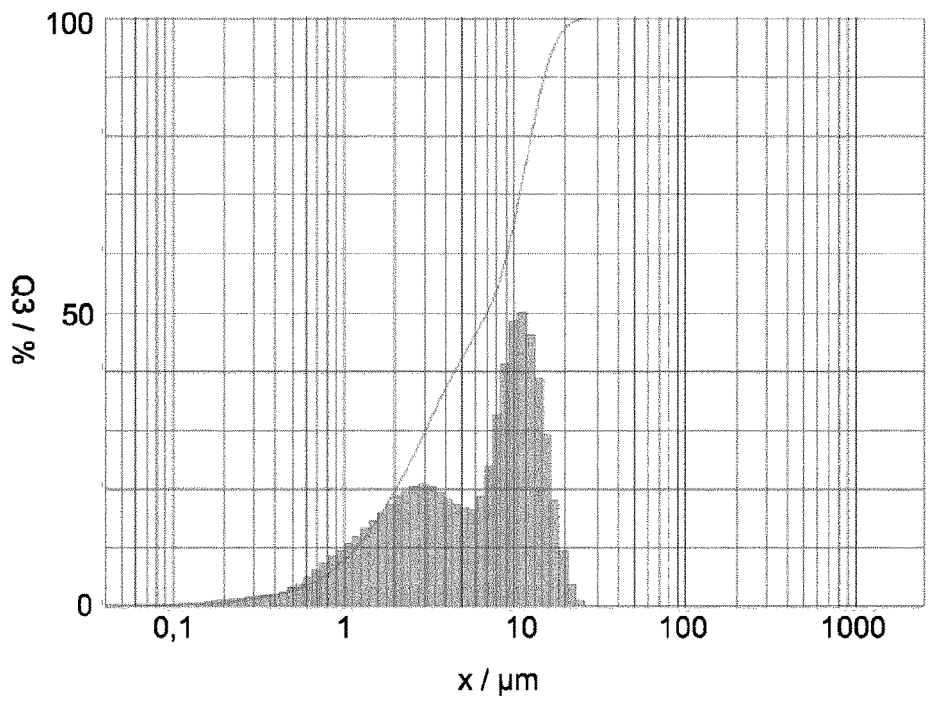

The matrix liquid subsequently to its manufacture was analysed with a laser diffraction system Cilas 1190 LD (Quantachrome). The grain sizes of the oil droplets containing CBD and present in the emulsion of the matrix liquid is represented in FIG. 5. The sum distribution curve with equivalent diameters $x_{10}$=1.18 μm, $x_{50}$=6.99 μm and $x_{90}$=15.17 μm has an average diameter of x=7.58 μm. Furthermore, the density distribution curve with its two maxima exhibits a bi-modal distribution.

After the manufacture of the cannabinoid granulate and a renewed dissolving of the cannabinoid granulate in water, a stable oil-in-water emulsion has formed in the aqueous environment.

Figure 6:
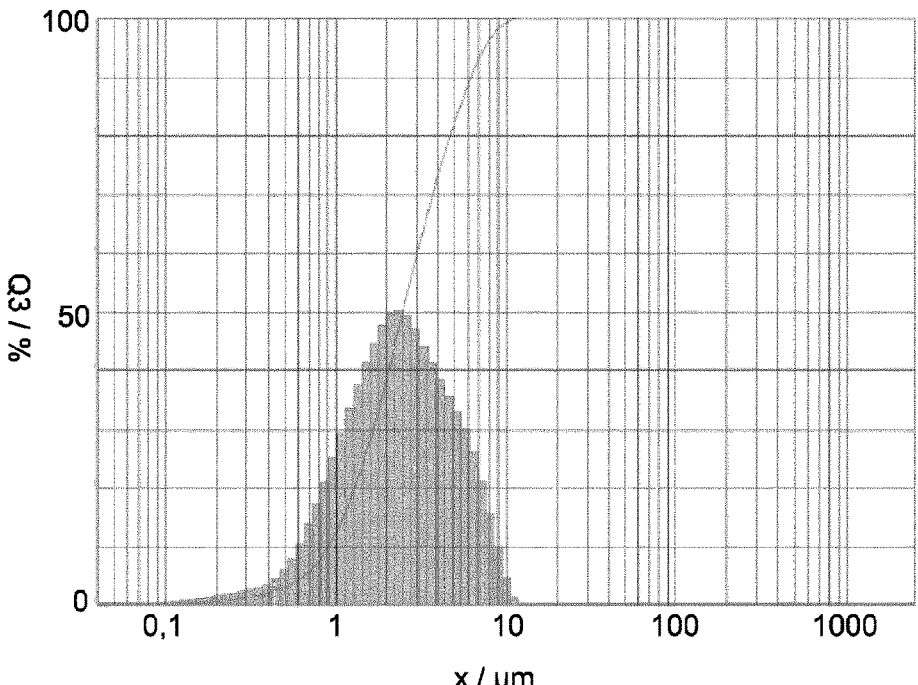

The cannabinoid granulates which are dissolved in the aqueous environment were dissolved in water and the grain size of the CBD-containing oil droplets was again analysed with the laser diffraction system Cilas 1190 LD (Quantachrome). FIG. 6 shows the analysis. Hereby, the sum distribution curve with equivalent diameters $x_{10}$=0.90 μm, $x_{50}$=2.48 μm and $x_{90}$=6.24 μm has an average diameter of x=3.08 μm. Furthermore, the density distribution curve displays a mono-modal distribution. The oil droplets exhibit a very homogenous density distribution with significantly lower diameters. This leads to a significantly improved resorbability of CBD and thus to a more optimal bioavailability of CBD. This improved resorbability of the cannabinoids results from the more homogeneous and smaller emulsion particles.

The invention claimed is:

1. A method for manufacturing a cannabinoid granulate which is essentially soluble in an aqueous environment, wherein a matrix liquid is manufactured from a first liquid which dissolves a cannabinoid or from a first liquid which dissolves a cannabinoid and a second liquid which with the first liquid forms an emulsion and from a cannabinoid which is dissolved in the first liquid or in the emulsion, wherein the matrix liquid is convectively dried in a fluidisation apparatus by way of spray granulation, spray agglomeration or spray encapsulation, into a cannabinoid granulate.

2. The method according to claim 1, wherein firstly a cannabinoid is dissolved in a first liquid and the first liquid subsequently mixed with the second liquid for forming the emulsion.

3. The method according to claim 1, wherein the first liquid is firstly mixed with the second liquid for forming the emulsion and a cannabinoid is subsequently dissolved in the emulsion.

4. The method according to claim 1, wherein the first liquid consists of the group of lipids, alcohols, oils and/or an arbitrary mixture of these.

5. The method according to claim 1, wherein the second liquid is an aqueous solution or water.

6. The method according to claim 1, wherein an emulsifier is added to the second liquid before the mixing with the first liquid.

7. The method according to claim 1, wherein an emulsifier is added to the emulsion before the convective drying.

8. The method according to claim 1, wherein an emulsifier is added to the matrix liquid preferably before the convective drying.

9. The method according to claim 1, wherein the matrix liquid is homogenised before the convective drying.

10. The method according to claim 1, wherein the matrix liquid is deposited onto one or more carrier substances before the convective drying in a fluidisation apparatus.

11. The method according to claim 1, wherein carrier particles are provided in the fluidisation apparatus.

12. The method according to claim 1, wherein additives are added to the solution, emulsion or matrix liquid before the convective drying.

13. An apparatus for use in the method of manufacturing a cannabinoid granulate which is essentially soluble in an aqueous environment according to claim 1, wherein the apparatus comprises a vessel system which comprises an inlet and a matrix liquid outlet, for the manufacture of the matrix liquid, and a convective drying apparatus which is fluidically connected to the matrix liquid outlet of the vessel system, wherein the convective drying apparatus is a fluidisation apparatus that dries the matrix liquid by way of spray granulation, spray agglomeration or spray encapsulation, into a cannabinoid granulate.

14. The apparatus according to claim 13, wherein the fluidisation apparatus is designed as a spouted bed apparatus or as a fluidised bed apparatus.

15. The apparatus according to claim 13, wherein the vessel system comprises one or more containers.

16. The apparatus according to claim 13, wherein the fluidisation apparatus comprises a nozzle for atomising the emulsion or solution.

17. The apparatus according to claim 13, wherein a homogeniser for homogenising the matrix liquid is arranged between the vessel system and the fluidisation apparatus.

18. The apparatus according to claim 13, wherein a granulation unit, selected from a high-shear granulator, a vertical granulator or a rotor disc granulator is arranged between the vessel system and the drying apparatus, for granulating the matrix liquid.

19. The method according to claim 1, wherein the fluidisation apparatus is selected from the group consisting of: a spouted bed apparatus and a fluidized bed apparatus.

* * * * *